United States Patent [19]
Burton et al.

[11] Patent Number: 5,998,155
[45] Date of Patent: Dec. 7, 1999

[54] STABLE COMPOSITION OF IMMOBILIZED PROTEIN HAVING AFFINITY FOR BIOTIN

[75] Inventors: Steven James Burton, Peterborough; James C. Pearson, Cambridge; Peter A. D. Edwardson, Chester, all of United Kingdom

[73] Assignee: E.R. Squibb & Sons, Inc., Princeton, N.J.

[21] Appl. No.: 08/904,368

[22] Filed: Aug. 1, 1997

Related U.S. Application Data

[62] Division of application No. 08/556,244, Nov. 9, 1995, Pat. No. 5,691,152.

[51] Int. Cl.[6] .................. C07D 235/02; C12N 11/00; C12N 11/10; G01N 33/569
[52] U.S. Cl. .................. 435/7.5; 435/178; 435/68.1; 435/174; 435/966; 435/967; 435/972; 548/303.7; 530/367
[58] Field of Search .................. 435/68.1, 7.5, 435/966, 967, 972, 174, 178; 548/303.7; 530/367

[56] References Cited

U.S. PATENT DOCUMENTS

| | | | |
|---|---|---|---|
| 3,779,706 | 12/1973 | Nablo | 21/54 R |
| 4,709,037 | 11/1987 | Sigler | 546/271 |
| 4,775,636 | 10/1988 | Moeremans et al. | 436/518 |
| 4,794,082 | 12/1988 | Sigler | 435/177 |
| 4,798,795 | 1/1989 | Sigler | 435/177 |
| 5,026,785 | 6/1991 | Mage et al. | 525/329.4 |
| 5,043,288 | 8/1991 | Motsenbocker | 436/518 |
| 5,068,198 | 11/1991 | Gibbons et al. | 435/7.1 |
| 5,126,241 | 6/1992 | Schenk | 435/7.1 |
| 5,168,049 | 12/1992 | Meade et al. | 435/69.1 |
| 5,306,824 | 4/1994 | Powers et al. | 548/304.1 |
| 5,691,152 | 11/1997 | Burton et al. | 435/7.5 |
| 5,739,288 | 4/1998 | Edwardson et al. | 530/382 |
| 5,750,657 | 5/1998 | Edwardson et al. | 530/382 |

FOREIGN PATENT DOCUMENTS

| | | |
|---|---|---|
| 0592242 | 8/1993 | European Pat. Off. . |
| 3629194 | 3/1987 | Germany . |
| 63-246382 | 2/1987 | Japan . |
| 458155 | 6/1990 | Japan . |

OTHER PUBLICATIONS

Updyke et al, "Immunoaffinity isolation of membrane antigens with biotinylated . . . ", 1984, 73(1), 83–95, see abstract only.

Delaage et al, "Immunoadsorbent with low levels of antibody release, and process . . . " Eur. Pat. Appl. 9 pp., see abst. only.

Bayer and Wilchek, *Journal of Chromatography*, "Application of avidinbiotin technology to affinity–based separations," 510 (1990) pp. 3–11.

*Primary Examiner*—David M. Naff
*Assistant Examiner*—Deborah K. Ware
*Attorney, Agent, or Firm*—Theodore R. Furman, Jr.; John M. Kilcoyne

[57] ABSTRACT

Compositions and methods for avidin or protein having affinity for biotin immobilized on an inert support material, e.g., agarose, are disclosed. The compositions have high activity levels for binding biotin and may include a bulking agent, e.g., maltose, and a protectant to maintain the stability and integrity of the composition during lyophilization and terminal sterilization processes. The compositions have applicability in any instance where avidin agarose and/or the avidin/biotin technology are useful. In particular, the present compositions are useful in an enzyme capture system to prepare fibrin monomers useful for fibrin sealants.

27 Claims, No Drawings

STABLE COMPOSITION OF IMMOBILIZED PROTEIN HAVING AFFINITY FOR BIOTIN

This is a divisional application of application Ser. No. 08/556,244, filed Nov. 9, 1995, now U.S. Pat. No. 5,691,152.

BACKGROUND

The avidin-biotin affinity-based technology has found wide applicability in numerous fields of biology and biotechnology since the pioneering work by Dr. Edward Bayer and Dr. Meier Wilchek in the 1970's. The affinity constant between avidin and biotin is remarkably high and is not significantly lessened when biotin is coupled to a wide variety of biomolecules. This affinity is substantially maintained even when derivatized forms of the biotin are employed and numerous chemistries have been identified for coupling biomolecules to biotin with minimal or negligible loss in the activity or other desired characteristics of the biomolecule. Originally applied to purification and localization procedures for biologically active macromolecules, avidin-biotin technology today has widespread use in medical diagnostics. Newer applications which continue to be developed include affinity targeting, cell cytometry, blotting technology, drug delivery, hybridoma technology, human stem cell selection and reinfusion as well as several approaches to enzyme capture. In some applications, avidin is immobilized onto an inert material over which a solution containing biotinylated biomolecules is passed. The affinity of the biotin for the avidin provides for the separation of the biomolecule from the solution. A review of the biotin-avidin technology can be found in *Applications of Avidin-Biotin Technology to Affinity-Based Separation*, Bayer, et al., *J. of Chromatography*, 1990, pgs. 3–11.

EP 592242 describes a novel fibrin sealant based on fibrin monomer as opposed to the traditional fibrinogen-based sealants and involves subjecting fibrinogen to a thrombin-like enzyme which is preferably removed after such treatment. EP 592242 describes that the enzyme capture and removal can be accomplished by using biotinylated batroxobin which can be recaptured with an avidin material. The fibrin monomer sealant described in EP 592242 is advantageously completely autologous. Since autologous fibrin sealants can not a-ways be prepared in advance, autologous processes which provide such sealants in short periods of time (i.e., less than one hour or preferably less than 30 minutes) from the patients' own blood provide a great advantage over current techniques and products. The steed with which such autologous processes can be carried out is dependent to a large degree on the activity of the biotin-and avidin-based reagents. Commercially available immobilized avidin typically contains about 200 to 400 biotin binding units (BBU) of activity (where 1BBU will bind 1 $\mu$g of $\alpha$-biotin) per gram of lyophilized powder (e.g., avidin on acrylic beads from Sigma) or about 20 to 50 BBU per milliliter of slurry or gel (e.g., avidin on agarose available from Sigma and Pierce).

Also, the above fibrin monomer technology and other biological applications would benefit from more convenient forms of avidin-and biotin-based reagents. For example, the processing necessary to prepare such compositions can have an adverse effect on the activity levels since many of the coupling/immobilization techniques involve materials which can significantly reduce these activities. Additionally, systems which reduce or eliminate leaching of avidin or of the avidin-biotin complexes would be advantageous in many applications. Further, many biological applications would be greatly enhanced by the availability of high activity avidin compositions which could be lyophilized and further, terminally sterilized while maintaining stability. Clearly, avidin compositions having higher avidin activity levels with greater stability, especially in freeze dried powder forms capable of withstanding terminal sterilization, e.g., gamma irradiation, would be an advance in the art.

SUMMARY OF THE INVENTION

In accordance with the present invention, stable, highly active compositions of avidin and an inert, easily separable support material such as a water soluble polymer, e.g., polysaccharides selected from agars and alginates, and having an activity level of 1000 BBU or more per gram of lyophilized form and 50 BBU or more per milliliter of slurry or hydrated gel, are disclosed. Preferred compositions include a bulking agent selected from nonionic water soluble polymers, a protectant, and the avidin/inert support material. These compositions may also include one or more materials selected to adjust and/or maintain the pH of the composition and are useful in an aqueous suspension or preferably in lyophilized form.

DETAILED DESCRIPTION OF THE PREFERRED EMBODIMENTS

Although avidin/inert support compositions are known, such compositions having the high levels of activity as described in this invention have not been heretofore disclosed. It has surprisingly been found that avidin compositions can now be prepared having activity levels multiples beyond those presently available without damaging the integrity and stability of the avidin or its inert support. Indeed, these compositions in any convenient form, i.e., slurry, suspension, hydrated gel, dehydrated gel, dried powders, etc., can be the basis of sterile, stable aqueous suspensions and remarkably stable lyophilized compositions capable of withstanding terminal sterilization e.g., gamma irradiation. The novel compositions herein have activity levels for lyophilized forms in excess of 1000 BBU (which is a measure of the biotin binding capability of the avidin composition as discussed above) and preferably between 1500 and 3000 BBU of activity and most preferably between 1800 and 2400 BBU of activity per gram of powder. In slurry, suspension or gel forms the novel avidin compositions of the present invention have activity levels in excess of 50 BBU and preferably between 75 and 150 BBU and more preferably between 90 and 110 BBU of activity per milliliter.

The preferred lyophilzed avidin/inert support compositions of the present invention are stable, can be terminally sterilized, have low moisture uptake/moisture content, reswell completely and rapidly upon reconstitution, are non-leachable and pharmaceutically acceptable. The bulking agents used in conjunction with this invention protect the gel bead from damage during the freeze drying process and provide for rapid and complete reswelling of the gel beads upon reconstitution of the freeze dried material. The unique combination of components herein also protects the avidin/inert support component from any deleterious effects upon terminal sterilization of the composition. Thus, the affinity of the avidin for biotinylated biomolecules is maintained even after these rigorous processing steps, i.e., lyophilization and/or terminal sterilization. Accordingly, in the various applications where the affinity characteristics of the avidin and the integrity of the inert support are both critical to the effectiveness of the avidin/biotin technology, a superior composition is provided by the invention.

The avidin component of the present invention refers to avidin, monomeric avidin, Streptavidin, other proteins having an affinity for biotin including derivatized forms of avidin and recombinant forms of any of the above. The avidin should be insoluble, which is preferred, or otherwise easily separable from the inert support using techniques such as emulsion/phase separation and the like. The inert support material is any material that has low reactivity, is hydrophilic, forms a porous or nonporous matrix which can be readily separated from a liquid phase of the reaction mixture when necessary. Such materials include, but are not limited to, dextran, cellulose, starch, carageenan, chitin, polyacrylamide, hydroxyethylmethacrylate, stryrenedivinylbenzene, oxiraneacrylic, silica, alumina, zirconia, glass, perfluorocarbons and polysaccharides from the agar family or the alginate family which form gel beads. These and other such materials are useful and well known as inert materials in separation columns. Most are commercially available, e.g., agarose which is preferred and which is available as Sepharose™ from Pharmacia.

The invention will be further described referring to avidin and agarose. It should be understood that avidin is meant to include any of the forms of avidin described hereinabove and agarose represents any of the inert support materials described hereinabove.

The bulking agent is a nonionic water soluble polymer. Examples include, but are not limited to, simple sugars (e.g., mono- and di-saccharides), oligosaccharides, polysaccharides, polyvinylpyrrolidone, polyvinylalcohol or polyethyleneglycol. Preferably, the bulking agent is a sugar ranging in molecular weight from that of glucose up to and including that of high molecular weight dextran. More preferably, the bulking agent is an oligosaccharide based on glucose such as dimeric glucose (i.e., maltose), trimeric glucose (maltotriose), maltotetraose, maltopentaose, maltohexaose, maltoheptaose, low molecular weight dextran, high molecular weight dextran including combinations of any of the above, with maltose being preferred.

The protectan: of the present compositions is selected from antioxidants, free radical scavengers and reducing agents. Preferred are antioxidants such as α-tocopherol, reduced glutathione, quinones, N, N-dimethyl-p-phenylenediamine, ascorbylpalmitate, amino acids, tartaric acid, phosphoric acid and ascorbic acid/sodium ascorbate with ascorbic acid/sodium, ascorbate being most preferred.

The present compositions may also include an agent to adjust the pH to a desired level. For example, alkaline materials, e.g., sodium hydroxide can be added to adjust the pH which is preferably at about 4 for use with biotinylated batroxobin. Further, buffers may be incorporated to maintain the pH level. Buffers and agents to adjust the pH are well known in the art and any such materials are suitable depending upon the application. In a preferred embodiment, the ascorbic acid protectant also serves as a buffer. However, it should be understood that any convenient buffer and pH can be utilized as required for the particular application.

The compositions of the present invention are conveniently in an aqueous slurry or suspension. Since these slurries or suspensions can either be prepared aseptically or can be terminally sterilized, they are also an integral part of this invention. Preferably, the aqueous slurries or suspensions of this invention are freeze dried since the lyophilized powders resulting therefrom are highly stable, terminally sterilizable (e.g., by gamma irradiation), non-hygroscopic and extremely easy to handle.

As the compositions of this invention deal, inter alia, with beaded gels in slurries or suspensions, it is important to clarify what some of these terms are understood to mean within this art. By way of example, agarose is commercially available in 4% and 6% gels. This refers to the fact that the hydrated gel bead material is, for example, 4% by weight of cross-linked agarose beads containing 96% by weight of water (i.e., within the bead) for the 4% gel and 6% by weight of cross-linked agarose beads containing 94% by weight of water for the 6% gel. The beads can be any convenient size and size range as are known and available in the art. The 4% and 6% gels available above typically comprise beads having a diameter range between 60 and 120 microns.

These gel beads, in turn, can be utilized in several forms. For example, a "wet settled gel" is obtained when the gel beads in water are allowed to settle out under gravity, i.e., by draining off most of the water, leaving only the hydrated gel beads and interstitial water, i.e., water between the beads. This typically results in a wet settled gel comprising 70–80% hydrated bead volume and 20–30% interstitial water volume, preferably about 75% by volume of hydrated beads about 25% by volume of interstitial water. The wet settled gel form is convenient to use in processing because the material is mostly water providing a density close to 1. This, in turn, provides flexibility in relatively accurate measuring either by weight or volume, especially when using larger quantities, i.e., 10 grams and above.

A "moist" or "sucked" gel comprises the hydrated gel beads with the interstitial water removed and is a more accurate way to measure smaller amounts of gel.

In the processing discussed below and in the Examples which follow, the agarose gel, agarose gel beads, agarose or agarose beads refers to a wet settled gel unless otherwise noted.

The aqueous composition of the present invention preferably comprises avidin agarose gel beads (wet settled gel) in a slurry or suspension with a solution comprising:

1 to 50% by weight of the bulking agent;

0.01 to 50% by weight of the protectant; and 40 to 98.99% by weight of water.

More preferably, the aqueous composition according to the present invention comprises avidin agarose gel beads in a slurry with a solution comprising:

5 to 40% by weight and most preferably 10% by weight of a bulking agent, preferably a sugar, more preferably maltose;

0.1 to 10% by weight and most preferably 1% by weight of a protectant, preferably an antioxidant, more preferably ascorbic acid; and 50 to 94.9% by weight of water;

and optically, in a preferred embodiment, further including:

an agent sufficient to adjust the pH to a desired level, preferably an alkaline material, e.g., sodium oxide to adjust the pH to about 4; and buffer, which is preferably the ascorbic acid protectant.

Typically the slurry or suspension comprises about 10 to about 70% by volume of wet settled gel beads in about 30 to 90% of one of the above "protectant" solutions, it being understood that compositions having 10% beads are in a suspension whereas those compositions having 70% beads are in the form of a slurry or even a gel.

In order to immobilize the avidin to a support, e.g., agarose, the support must be pre-activated prior to avidin coupling. A preferred process involves the use of epichlorohydrin as the activating agent, however, activation can be carried out by any suitable technique capable of providing an activated support which can form covalent bonds with avidin. For example, various activation reagents available for derivatizing supports are: diazonium groups, isocyanate groups, acid chloride groups, acid anhydride groups, sulfonyl chloride groups, dinitro fluorophenyl groups, isothiocyanate groups, hydroxyl groups, amino groups, n-hydroxysuccinmide groups, triazine groups, hydrazide groups, carbodiimide groups, silane groups, aldehydes, 1, 4-butanediol diglycidyl ether, sodium metaperiodate, 1, 1-carbonyl diimidazole, divinylsulphone, 2-fluoro-1-methylpyridinium toluene-4-sulphonate and cyanogen bromide. See (a) Pentapharm Patent DT 2440 254 A1; (b) P. D. G. Dean, W. S. Johnson and F. A. Middle (Editors) (1991) IRL Press Oxford—Affinity Chromatography—A practical approach—chapter 2—Activation Procedures and (c) C. R. Lowe and P. D. G. Dean (1974) John Wiley and Sons Ltd., London, Affinity Chromatography, the disclosures of which are incorporated herein by reference.

The preferred activation chemistry is by means of an epoxide group following activation with epichlorohydrin. The use of a support activated in this manner results in essentially no avidin leaching after avidin bonding.

Generally, the support is activated by a highly reactive compound, which subsequently reacts with a functional group of the ligand, e.g., —OH, —NH$_2$, —SH, —CHO, to form a covalent linkage. Remaining active groups, which have no avidin attached, can be, but it is not essential, blocked with compounds such as ethanolamine, acetic anhydride or glycine.

The preferred activation chemistries for use in the subject matter invention are:

(a) Activation of the support by epichlorohydrin or a bifunctional epoxide compound followed by coupling avidin via —NH$_2$, —SH or —OH groups.

(b) Cyanogen bromide activation followed by direct coupling of avidin via —NH$_2$ groups on the protein.

(c) Activation of the support with monochlorotriazine followed by coupling of avidin via —NH$_2$, —OH or —SH groups.

(d) Activation of the support with dichlorotriazine followed by coupling of avidin via —NH$_2$, —OH or —SH groups.

(e) Tresyl chloride activation of the support followed by coupling of avidin via —NH$_2$, —OH or —SH groups.

(f) Activation of the support with adipic acid hydrazide or hydrazide followed by coupling of oxidized avidin via —CHO groups.

(g) Activation of the support with an amino ligand followed by coupling of oxidized avidin via —CHO groups.

All the above preferred methodologies employ agarose as the support, however, it is possible to use other aforementioned supports as well. For example, when using silica, the preferred activation chemistries are:

(a) Activation of the support by ecichlorohydrin or a bifunctional epoxide compound followed by coupling avidin via —NH$_2$, —SH or —OH groups.

(b) Gamma - glycidoxypropyltrimethoxysilane activation with direct coupling of the avidin via —NH$_2$ groups on the protein.

(c) Cyanogen bromide activation followed by direct coupling of avidin via —NH$_2$ groups on the protein.

(d) Gamma-glycidoxytrimethoxysilane activation followed by opening of the epoxide ring to form a diol group, which can be subsequently activated with cyanogen bromide. Direct coupling of the avidin can be achieved via —NH$_2$, groups on the protein.

(e) Gamma-glycidoxycropyltrimethoxysilane activation followed by preparation of amino-silica by treatment with ammonia solution.

The amino-silica can be subsequently activated with cyanuric chloride (triazine) and the avidin coupled via —NH$_2$, —OH or —SH groups.

Coupling of the avidin to the activated support must be buffered at a certain pH to obtain optimal avidin binding. Generally, with standard activation techniques such as gamma -glycidoxypropyltrimethoxysilane coupling of avidin to activated support and cyanogen bromide coupling of any protein to active groups requires buffering at a pH 1–2 units higher than the pKa of the primary and secondary amines of the avidin. However, the use of cyanuric chloride as the activator enables the use of much lower pH buffers (optimal coupling pH is 4–6). Another method of coupling avidin to an inert support is via its carbohydrate-moietes. This involves first the oxidation of the sugar group to —CHO groups followed by direct coupling a acid pH to an amino group such as hydrazide. A wide range of coupling buffers can be used. See, for example, Table 1.

TABLE 1

EXAMPLES OF COUPLING BUFFERS USED IN AVIDIN IMMOBILIZATION TO SILICA AND AGAROSE SUPPORTS

| SUPPORT | ACTIVATION METHOD | COUPLING BUFFER |
| --- | --- | --- |
| Silica | gammaglycidoxypropyltrimethoxysilane | 0.1M Sodium bicarbonate pH 8–9 10 mM HEPES pH 7.0 |
| Silica | Y-glycidoxypropyltrimethoxysaline + cyanogen bromide | 0.1M Sodium bicarbonate pH 8–9 10 mM HEPES pH 7.0 |
| Silica | Cyanogen Bromide | Water pH 7.0 0.1M Sodium bicarbonate pH 7–9 10mM HEPES pH 7.0 |
| Agarose | Monochlorotriazine | 50 mM Sodium Acetate/1MNaCl pH 4.0 |
| Agarose | Dichlorotriazine | 0.1M Potassiurn phosphate/1MNaCl pH 8.0–9.0 |
| Agarose | Tresyl chloride | 50 mM Potassium phosphate/0.5M NaCl pH 7.7 |
| Agarose | Hydrazide | 50 mM Sodium Acetate pH 5.5 10 mM NaBH$_4$ |

TABLE 1-continued

EXAMPLES OF COUPLING BUFFERS USED IN
AVIDIN IMMOBILIZATION TO SILICA AND AGAROSE
SUPPORTS

| SUPPORT | ACTIVATION METHOD | COUPLING BUFFER |
|---|---|---|
| Agarose | Amine | 50 mM Sodium Acetate pH 5.5 10 mM NaBH$_4$ |
| Agarose | Epoxide | 20 mM Sodium Bicarbonate/0.5M NaCl pH 10.0 |

As described previously, these "high activity" compositions of avidin immobilized on an inert support, e.g., agarose, are useful in any and all chemical and biological applications where present avidin technology is useful. In a preferred embodiment, the avidin immobilized onto agarose is thereafter incorporated into composition of this invention conveniently by mixing the various components in wager or by mixing the "protectant" solution components in water and thereafter adding the avidin agarose gel. For situations requiring a sterile aqueous composition this can be carried out aseptically or preservatives can be added to the composition. Preferably, the aqueous composition is lyophilized into a powder form which can be terminally sterilized, e.g., by gamma irradiation. Any convenient freeze-drying process can be employed. A preferred process involves cooling the aqueous composition in a lyophilization apparatus to about −33° C. and maintaining this while a vacuum is initiated and the composition is dried under a reduced pressure of about 0.3 mbar. Thereafter, the composition is allowed to warm to room temperature.

The compositions of this invention involving the use or stable avidin compositions for the capture of a biotinylated form of thrombin or a thrombin-like enzyme, e.g., Batroxobin, are useful in methods to convert fibrinogen, or a fibrinogen-containing composition, into fibrin monomer, or a fibrin monomer-containing composition. Accordingly, the present invention further includes a novel method, to prepare a fibrin monomer useful, for example, in preparing a fibrin sealant. This novel method involves subjecting a source of fibrinogen to a biotinylated thrombin or thrombin-like enzyme composition to convert fibrinogen into fibrin monomer, "capturing" the biotinylated enzyme with an avidin composition of this invention to form a biotin/avidin complex, and removing the enzyme which is a part of the so-formed biotin/avidin complex.

The compositions of the present invention can further be incorporated into a processing unit, e.g., an automated centrifuge for preparing fibrin monomer as defined above. The avidin agarose composition can be preloaded into the processing unit in powder form or can be lyophilized in situ in the device or in a controlled release compartment of the device.

EXAMPLE 1
Aqueous Composition

Approximately 3.5 liters of beaded agarose gel (grade 4XL commercially available as Sepharose CL-4B™ from Pharmacia Co.) was gravity settled in a filter funnel. Approximately 2.8 liters of the so-settled agarose gel was transferred to a reaction vessel. The agarose gel was washed 12 times with 2.8 liter volumes of water. The so-washed gel was thereafter mixed with 2016 milliliters of 0–11 Molar sodium hydroxide and then reacted with 202 milliliters of epichlorohydrin for about 3 hours while maintaining 40° C. This activated gel was then washed with water and thereafter coupled to 19.6 grams of avidin in the presence of a sodium chloride/sodium bicarbonate pH 10 buffer at about 40° C. for 48 hours. The avidin-agarose gel was thereafter washed several times with sodium chloride solution and any unreacted epoxide groups were blocked by treatment with 1 M ethanolamine (pH 9.5) for 16 hours at 20° C. The avidin-agarose gel was next washed with water and thereafter mixed with an equal volume (28 L) of a solution containing maltose (20% w/v) and ascorbic acid (2% w/v) at pH 4.0 and allowed to drain under gravity.

EXAMPLE 2
Lyophilized Composition

The end-product provided by the method of Example 1, above, was placed on trays and loaded into a EF6(S) lyophilization apparatus (available from Edwards High Vacuum Co.) In which the shelves had been pre-cooled to −37° C. The avidin agarose slurry was cooled to −33° C. and the pressure was reduced (by vacuum) to 0.3 millibars. The product was maintained at this pressure and temperature until all of the ice had sublimed (about 70 hours). The pressure was then adjusted to 0.08 millibars and the temperature was raised steepwise 5° C. per hour to 30° C. to provide the lyophilized product.

We claim:

1. A stable composition of avidin, or a protein having an affinity for biotin, immobilized on an inert support material comprising:

an immobilized avidin or protein having an affinity for biotin/inert support component;

a bulking agent selected from nonionic water soluble compounds; and a protectant.

2. The composition of claim 1 in the form of an aqueous slurry or suspension.

3. The composition of claim 1 optionally including an agent to adjust the pH of the composition to a desired level.

4. The composition of claim 1 optionally including a buffer agent to maintain the desired pH of the composition.

5. The composition of claim 4 wherein said protectant also functions as a buffer.

6. The composition of claim 1 wherein the avidin can be monomeric avidin, Streptavidin, an avidin derivative, or a recombinant form of any of these, and the protein having an affinity for biotin can be a recombinant form thereof.

7. The composition of claim 1 wherein said inert support material is a hydrophilic material capable of forming a polymer matrix and which is separable from a liquid phase.

8. The composition of claim 7 wherein said inert support material is selected from the group consisting of dextran, cellulose, starch, carageenan, chitin, polyacrylamide, hydroxyethylmethacrylate, stryrenedivinylbenzene, oxiraneacrylic, silica, alumina, zirconia, glass, perfluorocarbons and polysaccharides from the agar and alginate families.

9. The composition of claim 7 wherein said inert support material is a polysaccharide selected from agars and alginates.

10. The composition of claim 8 wherein said inert support material is agarose.

11. The composition of claim 10 wherein said agarose is in the form of gel beads.

12. The composition of claim 1 wherein said bulking agent is selected from the group consisting of simple sugars, oligosaccharides, polysaccharides, polyvinylpyrrolidone, polyvinylalcohol and polyethyleneglycol.

13. The composition of claim 12 wherein said bulking agent is a sugar ranging in molecular weight from that of glucose up to and including that of high molecular weight dextran.

14. The composition of claim 13 wherein said bulking agent is an oligosaccharide based on glucose.

15. The composition of claim 14 wherein said bulking agent is selected from the group consisting of dimeric glucose, trimeric glucose, maltotetraose, maltopentaose, maltohexaose, maltoheptaose, low molecular weight dextran, high molecular weight dextran and combinations of any of the above.

16. The composition of claim 1 wherein said protectant is selected from the group consisting of antioxidants, free radical scavengers and reducing agents.

17. The composition of claim 16 wherein said protectant is an antioxidant selected from the group consisting of α-tocopherol, reduced glutathione, quinones, N, N-dimethyl-p-phenylenediamine, ascorbylpalmitate, amino acids, tartaric acid, phosphoric acid and ascorbic acid/ sodium ascorbate.

18. The composition of claim 3 including an alkaline material to adjust the pH to about 4.

19. The composition of claim 18 wherein said alkaline material is sodium hydroxide.

20. The composition of claim 5 wherein the protectant is ascorbic acid.

21. The aqueous composition of claim 2 comprising avidin agarose gel beads in a slurry or suspension with a solution comprising:

to 50% by weight of a bulking agent;

0.01 to 50% by weight of a protectant; and 40 to 98.99% by weight of water; and optionally, materials to adjust and/or maintain a desired pH.

22. The composition of claim 21 comprising avidin agarose gel beads in a slurry or suspension with a solution comprising:

5 to 40% by weight of said bulking agent;

0.1 to 10% by weight of said protectant; and 50 to 94.9% by weight of water.

23. The composition of claim 22 comprising avidin agarose gel beads in a slurry or suspension with a solution comprising:

about 10% by weight of maltose;

about 1% by weight of ascorbic acid; and sodium hydroxide sufficient to provide a pH of said composition of about 4.

24. The composition of claim 1 in lyophilized form.

25. In a method employing avidin/biotin affinity the improvement comprising using the composition of claim 1.

26. A method for terminal sterilization of avidin immobilized on an inert support material which provides sterility for a composition while maintaining stability and biotin affinity which method comprises subjecting a composition of claim 1 to a terminal sterilization process.

27. The method of claim 23 wherein said avidin agarose in a lyophilized form.

* * * * *